United States Patent [19]

Vaillancourt

[11] Patent Number: 5,290,254
[45] Date of Patent: Mar. 1, 1994

[54] SHIELDED CANNULA ASSEMBLY

[76] Inventor: Vincent L. Vaillancourt, 14 Bunyan Dr., Livingston, N.J. 07039

[21] Appl. No.: 976,464

[22] Filed: Nov. 16, 1992

[51] Int. Cl.$^5$ ............................................... A61M 5/32
[52] U.S. Cl. .................................... 604/192; 604/198; 128/919
[58] Field of Search ............... 604/198, 192, 187, 263, 604/110, 905; 128/919

[56] References Cited

U.S. PATENT DOCUMENTS

| | | | |
|---|---|---|---|
| 2,847,995 | 8/1958 | Adams | 604/905 X |
| 3,134,380 | 5/1964 | Armao | 604/198 |
| 3,354,881 | 11/1967 | Bloch | 604/198 |
| 4,564,054 | 1/1986 | Gustavsson | 604/198 X |
| 4,725,267 | 2/1988 | Vaillancourt | 604/192 |
| 4,775,369 | 10/1988 | Schwartz | 604/263 |
| 4,846,809 | 7/1989 | Sims | 604/198 |

*Primary Examiner*—John D. Yasko
*Attorney, Agent, or Firm*—Francis C. Hand

[57] ABSTRACT

The shielded cannula assembly includes a tubular shield of latex rubber which is mounted over the cannula of the assembly. The shield includes a resilient collapsible tubular portion which is able to collapse in an accordion-like manner when a longitudinal force is imposed thereon. The shield also has a cap at the distal end which seals off a chamber in which the cannula is contained in a sterile manner. The cap includes a transverse wall which may be pierced by the cannula when the cannula is passed into a vial of medication or into a connector of an administration set.

19 Claims, 2 Drawing Sheets

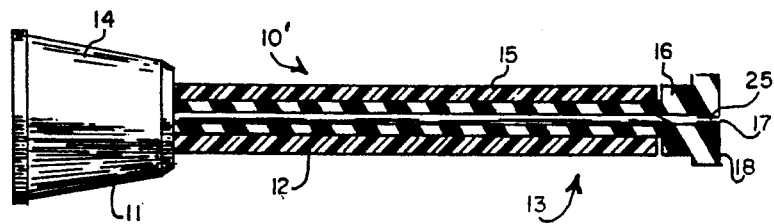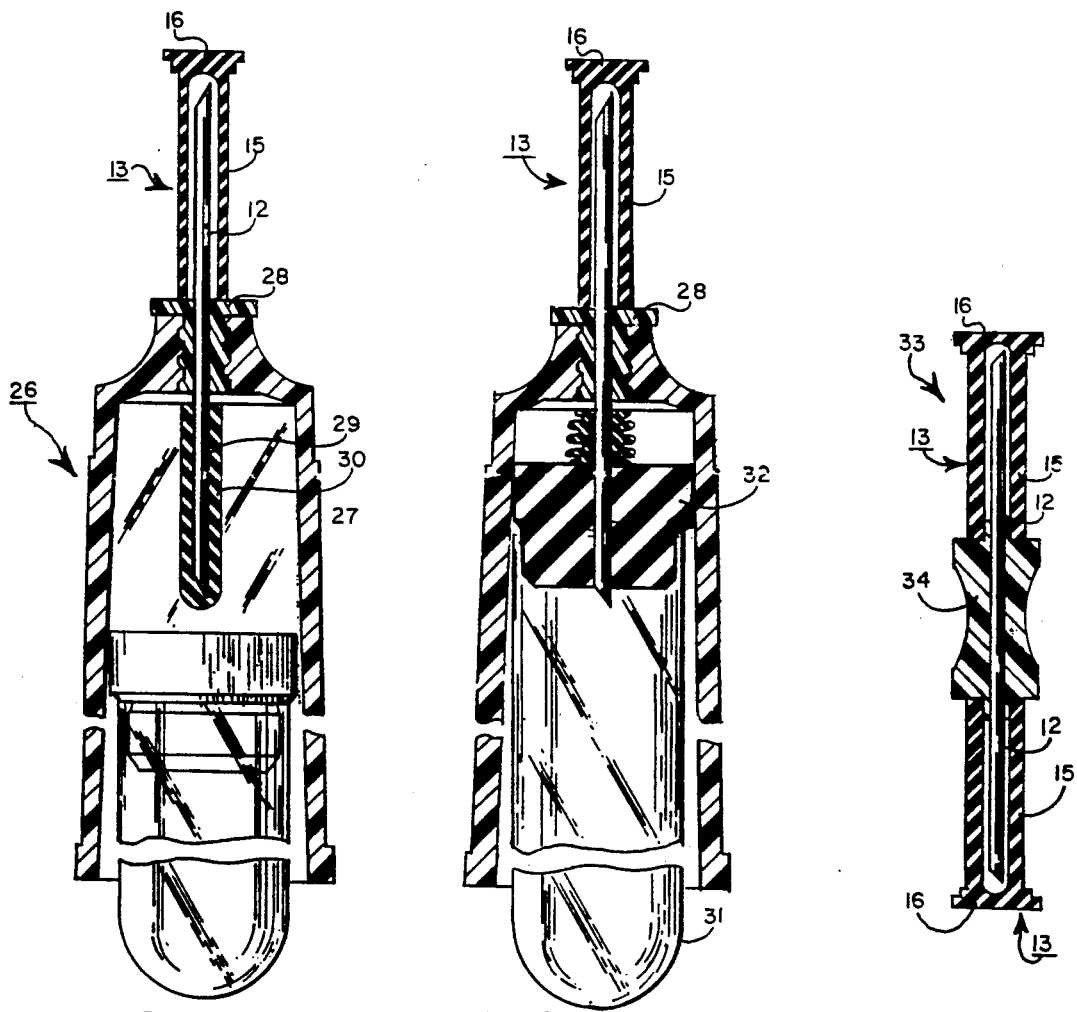

SHIELDED CANNULA ASSEMBLY

This invention relates to a shielded cannula assembly.

As is known, one major problem with a hypodermic needle as well as other needles is the threat of cutting oneself or another thereby exposing a blood vessel to the environment. This has become especially important in a hospital atmosphere where AIDS patients or AIDS members of the staff can infect others by having their blood interact, for example, by touching another person.

Various techniques have been forwarded to overcome this problem. These techniques include placing a shield over the needle after use; allowing for only a one time use of the needle with an automatic covering system which prevents further use, and various types of means for remotely shielding the needle after use. However, in none of these cases does the needle remain totally protected during an entire procedure. Further, if the needle is used twice, there is no provision to handle more than one use of the needle.

In practice, needles are almost always used at least twice. That is, in a first use of a needle which is attached to a syringe (a majority of the needle usage), the needle is used to puncture a drug vial and, if already constituted, draw the drug (or other medication) into the syringe. If the drug has not been reconstituted, for example, being in a powder state, then the needle must be used to reconstitute the drug. Once the syringe has been filled with medication and is otherwise ready for use on a patient, the needle of the syringe is used to pierce a septum on an I.V. Administration Set or to alternately puncture the body of the patient directly. This is followed by the administration of the drug. The needle is then withdrawn and the exposed needle is, in some fashion, shielded and ultimately discarded.

It has also been known, for example from U.S. Pat. No. 5,122,123 and 4,449,539 to mount a hollow needle within a female connector of a connector assembly in a recessed manner so as to prevent sticking. In addition, it has been known to mount a collapsible tube within the female connector about the hollow needle with a membrane at one end in order to form a sealed chamber to maintain the hollow needle in a sterile condition. When a male connector is inserted into the female connector, the tube is to be collapsed with the hollow needle piercing through the membrane.

Accordingly, it is an object of the invention to provide a cannula of an assembly with a continuous type of protection.

It is another object of the invention to render a hypodermic needle "stickless".

It is another object of the invention to provide a relatively simple structure for maintaining a cannula, such as a hypodermic needle in a closed system during use and when not in use.

It is another object of the invention to avoid contamination of the contents of a medicant or fluid containing vial, canister, bottle or the like due to repeated withdrawal of its contents via hypodermic needles and the like.

It is another object of the invention to provide a relatively simple structure to secure a hypodermic needle in a shielded condition from one use to another use as well as in between uses.

Briefly, the invention provides a shielded cannula assembly which comprises a housing, a hollow cannula mounted in and extending from the housing and a tubular shield extending from the housing about the cannula.

The housing is constructed in any suitable manner. For example, the housing may be in the form of a female luer hub for fitting on a syringe or other container which defines a chamber, for example, for receiving medications, fluids and the like. The housing may itself define a chamber to receive fluids. The hollow cannula which may be in the form of a hypodermic needle has a lumen which is in communication with the chamber of the housing in order to conduct the medication or fluid into or from the chamber as the case may be.

In accordance with the invention, the tubular shield which is exposed to the environment has a resilient longitudinally collapsible tubular portion concentrically about the cannula and a transverse wall at a distal end to form a sealed chamber with the tubular portion so as to contain the cannula therein in a sterile condition. This wall is made of a material to permit penetration of the cannula therethrough in response to longitudinal collapsing of the tubular portion. The material is also such as to reseal in response to expansion of the tubular portion and withdrawal of the cannula from the wall.

The tubular shield can be made so that the tubular portion and wall are integral. For example, the shield may be formed from a one-piece body made of an elastomeric material such a latex rubber.

The distal wall of the tubular shield is formed so as to have a flat face, for example, for abutting a septum of a vial containing a fluid. In this case, the face of the shield can be brought up against the septum of the vial and thereafter the cannula injected through the wall and septum into the interior of the vial for withdrawing fluid or medication therefrom. Upon removal from the vial, the tubular portion of the shield expands resiliently back to the normal condition so that the transverse wall again forms a sealed chamber relative to the cannula. In this way, the cannula is maintained in a closed system at all times. Furthermore, by maintaining the cannula in a closed system, that is, in a sterile condition, no contamination is introduced into the vial. Thus, contamination of the contents of the medicant or fluid containing vial is avoided even after repeated withdrawal of the contents of the vial using one or more cannulae of this type.

The tubular shield is constructed so as to allow the tubular portion to readily collapse when a longitudinal force is imposed upon the flat face of the transverse wall. In addition, the transverse wall is made part of a rigid cap which forms the end of the shield. Such a rigid cap serves to protect against the inadvertent passage of the free distal end of a hypodermic needle therethrough. That is, the rigid cap serves to protect against inadvertent passage of a sharp end of a needle through a side wall during transportation from place to place. In this respect, the cap can be made with an outside diameter greater than the outside diameter of the tubular portion.

In one embodiment, the transverse wall of the cap is sized of a thickness to permit penetration of the sharp end of a hypodermic needle therethrough in response to a longitudinal collapsing of the tubular portion of the shield while also permitting the resealing of the wall in response to expansion of the tubular portion and withdrawal of the needle therefrom.

In another embodiment, the transverse wall of the cap is provided with a slit to permit penetration of a non-cutting edge of a cannula such as a plastic or metal blunt cannula in response to a longitudinal collapsing of the tubular portion of the shield while also permitting the resealing of the wall in response to expansion of the tubular portion and withdrawal of the cannula therefrom.

The shielded hypodermic needle assembly may also be provided with a rigid sleeve which is removably mounted about the tubular portion in order to prevent longitudinal collapsing of the tubular portion when not in use. For example, the sleeve may be longitudinally split so as to be readily fitted over the tubular portion when the cannula assembly is not in use.

The cannula assembly can be used in a generally conventional manner. In this respect, the rigid sleeve, if present, is removed. The cannula can then be passed through the transverse wall of the shield into a drug vial to receive medication or connected to a connector of an administration set which is, in turn, connected to a patient in order to dispense medication. At this time, the tubular portion collapses in an accordion-like manner. When the cannula is withdrawn from the drug vial or administration set connector, the tubular portion springs back into an extended position so as to again completely encircle the cannula.

If the cannula assembly is to be transported from place to place, the rigid sleeve may be slipped over the tubular portion to maintain a positively locked condition which prevents the tubular portion from collapsing in an accordion-like manner.

The cannula assembly is otherwise of conventional construction, for example, employing a syringe which defines the housing in which the hollow cannula is mounted.

Further, the tubular shield may be constructed in a manner so as to be retrofitted onto existing syringes or made separately from a syringe.

These and other objects and advantages of the invention will become more apparent from the following detailed description taken in conjunction with the accompanying drawings wherein:

FIG. 7 illustrates a part cross-sectional view of a shielded cannula assembly employing a blunt cannula in accordance with the invention;

FIG. 8 illustrates a cross-sectional view of a further embodiment of a shielded assembly in accordance with the invention;

FIG. 9 illustrates a the shielded assembly of FIG. 8 in use with a blood collecting tube; and FIG. 10 illustrates a transfer needle embodiment in accordance with the invention.

Figure 1:
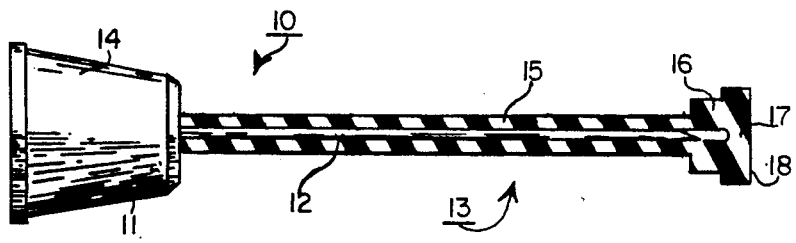
FIG. 1 illustrates a part cross-sectional view of a shielded hypodermic needle assembly in accordance with the invention.
Figure 3:
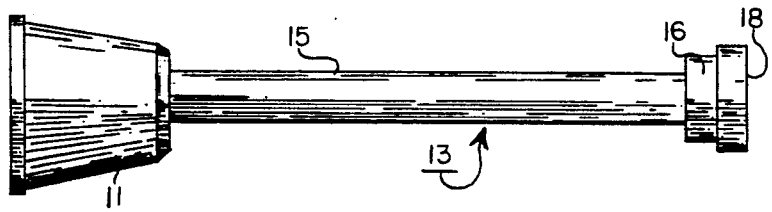
FIG. 3 illustrates the tubular shield in an extended position corresponding with FIG. 1.

Referring to FIGS. 1 and 3, the shielded cannula assembly 10 includes a housing 11, a hollow hypodermic needle 12 mounted in and extending from the housing 11 in conventional manner and a tubular shield 13 extending from the housing 11 concentrically about the needle 12.

The housing 11 is formed, for example, as a female luer hub with a chamber 14 which may be connected to a syringe (not shown) having a suitable chamber for receiving medications, fluids and the like.

The hypodermic needle 12 has a proximal end which is in communication with the chamber 14 in order to conduct the medication or fluid to and from the chamber 14 as is known.

The tubular shield 13 is exposed to the environment and is formed with a resilient longitudinally collapsible portion 15 and a cap 16 at the distal end of the tubular portion 15. As indicated, the tubular portion 15 is of constant outside diameter and is disposed concentrically about the hollow needle 12 and is of relatively thin thickness to permit longitudinal collapsing while being relatively thicker than the outside diameter of the needle 12 to be protective. The cap 16 is relatively rigid relative to the collapsible tubular portion 15 and has an outside diameter greater than the outside diameter of the tubular portion. As shown in FIG. 1, the cap 16 has a T-shaped cross-section. In addition, as indicated in FIG. 1, the cap defines a transverse wall 17 at the distal end of the shield 13 in order to form a sealed chamber with the tubular portion 15 in order to contain the needle 12 therein in a sterile condition.

The transverse wall 17 is made of a thickness and of a material to permit penetration of the sharp end of the needle 12 therethrough in response to longitudinal collapsing of the tubular portion 15. The transverse wall 17 is also of a nature to reseal in response to withdrawal of the needle therefrom, for example, upon expansion of the tubular portion 15 into the condition illustrated in each of FIGS. 1 and 3.

Figure 2:
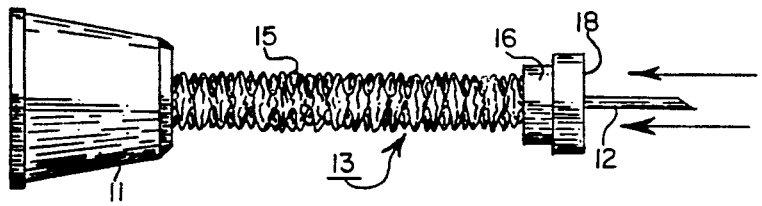
FIG. 2 illustrates a view of the assembly of FIG. 1 with the tubular shield in a partially collapsed state to expose a needle.

As shown in FIG. 2, when a longitudinal force F is imposed upon the cap 16, the tubular portion 15 collapses in an accordion-like manner so as to permit passage of the needle 12 through the transverse wall 17 of the cap 16.

The transverse wall 17 of the cap 16 is formed to have an uninterrupted flat end face 18 for purposes as explained below. This flat free end face 18 of the tubular shield 13 may also be provided with a coating, such as a silver antimicrobial coating or other anti-microbial coating to render the surface free of micro-organisms. Alternatively, the cap 16 may be formed to have a silver anti-microbial powder therein. In this manner, sterile type connections may be made without recourse to wiping the surfaces with a suitable antiseptic, such as pividone-iodine prior to use of the assembly.

As indicated in FIG. 1, the tubular portion 15 and cap 16 are integral, that is, made of one piece. Further, the tubular shield 13 may be made of any suitable material, such as latex rubber, to impart resiliency to the tubular portion 15 so as to permit collapsing into a collapsed condition as shown in FIG. 2 and springing back into an extended position as illustrated in FIG. 3. In addition, the material should be such as to permit the needle 12 to pierce through the transverse wall 17 while also permitting the wall 17 to reseal upon withdrawal 12.

Figure 4:
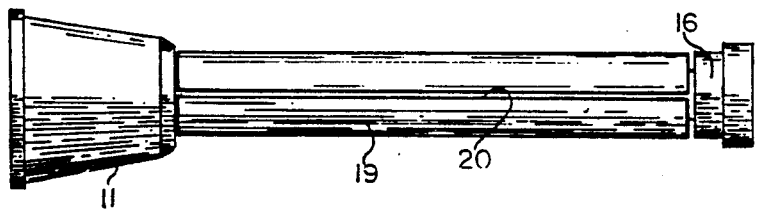
FIG. 4 illustrates a view similar to FIG. 3 of a hypodermic needle assembly employing a rigid sleeve about the tubular portion in accordance with the invention.
Figure 5:
FIG. 5 illustrates a cross-sectional view of the rigid sleeve of FIG. 4.

Referring to FIGS. 4 and 5, the needle assembly 10 may also be provided with a rigid sleeve 19 which serves to prevent longitudinal collapsing of the tubular portion 15 of the shield 13 when not desired. For example, the rigid sleeve 19 is provided with a longitudinal split 20 so as to be removably mounted about the tubular portion 15.

Figure 6:
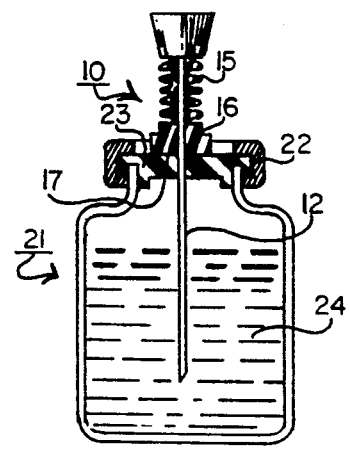
FIG. 6 illustrates a cross-sectional view of the shielded hypodermic needle assembly during introduction into a vial of medication.

Referring to FIG. 6, hypodermic needle assembly may be utilized to withdraw a fluid such as an anesthetic from a vial 21 while maintaining a sterile condition not only of the needle 12 but also of the contents of the vial 21. For example, the vial 21 may be provided with a cap 22 having a septum 23 across an opening thereof. Typically, the cap 22 would be sealed in hermetic manner relative to the vial 21 so as to maintain a contents 24 of the vial in a sterile condition.

When it is desired to remove some of the contents 24 from the vial 21, the needle assembly 10 is brought into abutment with the septum 23 so that the flat face 18 of the cap 16 is in face to face contact with the septum 23. At this time, if the cap 16 has not been provided with an antimicrobial coating, the face 18 of the cap 16 may be wiped with a suitable antiseptic along with the face of the septum 23.

Next, the needle 12 is pushed into the vial 21 so that the needle 12 passes through the transverse wall 17 of the shield 13 and the septum 23 of the vial 21. During this time, the relatively rigid block-like cap 16 provides a relatively large end face 18 which can be seated against the septum 23 of the vial 21 so that an effective seal can be maintained between the cap 16 and septum 23 during penetration of the needle 12 through the septum 23 under the spring-like force generated by the collapse tubular portion 15. After withdrawal of the antiseptic, the needle 12 can be withdrawn from the vial 21. At this time, the tubular portion 15 of the shield 13 springs back so that the transverse wall 17 again seals the chamber containing the needle 12. Thus, the needle 12 is maintained in a closed system at all times.

Since the needle 12 is not exposed to atmosphere there is little risk of contamination of the needle 12. Thus, the needle 13 can be reinserted into the vial 21 time and time again without risk of carrying contaminants into the contents 24 of the vial 21.

The tubular shield 13 can be readily made of any suitable material. However, latex rubber is preferred. Further, the transverse wall 17 of the cap 16 may be pre-slit in order to facilitate passage of the hollow needle 12 therethrough.

Referring to FIG. 7, wherein like reference characters indicate like parts as above, the shielded cannula assembly 10' is formed with a blunt ended cannula 12' of plastic or metal. In addition, the transverse wall 17 of the cap 16 is provided with a slit 25 in order to facilitate passage of the blunt end of the cannula 12' therethrough. In other respects, the assembly 10' functions and is used in the same manner as the embodiment described above with respect to FIGS. 1 to 5.

Referring to FIG. 8, wherein like reference characters indicate like parts as above, the cannula assembly 26 may be constructed, for example, for use in collecting blood. As shown, the assembly includes a housing 27 of cup shape, a hub 28 which is integral with the housing 27, a hollow cannula 12, as above, which extends from one end of the hub 28 and a second cannula 29 which extends from an opposite end of the hub 28 in a recessed manner within the housing 27. In addition, a tubular shield 13 is disposed about the cannula 12 while a one-way rubber valve 30 is mounted on the hub 28 and disposed about the second cannula 29 within the housing 27. This valve 30 may be constructed in the same fashion as the tubular shield 13 or may be constructed simply as a sleeve which is able to collapse about the cannula 29 while permitting the cannula 29 to pass therethrough.

The assembly 26 may be used, for example, as shown in FIG. 9 with a blood collecting tube to collect blood from a patient. As indicated, the blood collecting tube 31 is of conventional structure having a rubber stopper 32 or the like at one end to seal the contents of the tube 31. In addition, the tube is under vacuum.

When in use, the housing 27 of the assembly is fitted over the end of the blood collecting tube 31 and the cannula 29, such as a sharp ended needle, is pierced through the stopper 32 into the interior of the tube 31. At this time, the one-way rubber valve 30 collapses in an accordion-like manner to maintain a seal between the stopper 32 and hub 28 so that the vacuum is maintained through the cannula 29. Thereafter, the cannula 12 can then be connected to a suitable connector which, in turn, is connected to a vein of a patient to permit blood to be withdrawn under the vacuum pressure into the tube 31. Alternatively, the cannula 12 may communicate with the vein of a patient in other manners. In any event, during this time, the tubular portion 15 of the shield 13 would collapse while the cannula 12 is passed through the cap 16.

Referring to FIG. 10, the shielded assembly may be used as a transfer needle assembly 33. In this respect, a pair of cannulae 12 are mounted at opposite ends of a common housing 34 with the lumen of the cannulae 12 in communication. In addition, a shield 13 is mounted over each cannulae 12 and is mounted on the housing 34 in any suitable manner. Such a transfer needle 33 may be used, for example, for transferring fluid from one container to another container, for example, from one vial to another vial.

The invention thus provides a cannula assembly which maintains a hollow cannula in a closed system at all times.

Further, the invention provides a shielded hypodermic needle assembly which is able to avoid contamination of the contents of a fluid containing vial or bottle due to repeated withdrawal of the contents of the vial using the hypodermic needle or needles.

Further, the invention provides a shielded cannula assembly which can be employed in various manners such as on a syringe to protect a hypodermic needle extending therefrom, in a blood collecting container, and a transfer needle assembly for transferring fluid, or gases, from one container or vial to another container or vial.

What is claimed is:

1. A shielded cannula assembly comprising
a housing;
a hollow cannula mounted in and extending from said housing, said cannula having a lumen for passage of a fluid therethrough; and
one-piece tubular shield extending from said housing in an exposed manner relative to the surrounding environment, said shield consisting of a resilient longitudinally collapsible tubular portion concentrically about said cannula and a transverse wall at a distal end to form a sealed chamber with said tubular portion to contain said cannula therein in a sterile condition, said tubular portion being collapsible from an extended position about said cannula under a longitudinally applied force into a collapsed condition and being resiliently expandable into said extended position upon release of said force, said wall having an uninterrupted end face and being made of a material to permit penetration of said cannula therethrough in response to longitudinal collapsing of said tubular portion and resealing of said wall in response to expansion of said tubular portion and withdrawal of said cannula therefrom.

2. A shielded cannula assembly as set forth in claim 1 wherein said tubular portion and said wall are integral.

3. A shielded cannula assembly as set forth in claim 2 wherein said shield is made of latex rubber.

4. A shielded cannula assembly as set forth in 1 wherein said wall has a flat end face for abutting a septum of a vial containing fluid.

5. A shielded hypodermic needle assembly as set forth in claim 1 which further comprises a longitudinally split rigid sleeve removably mounted about said tubular portion to prevent longitudinal collapsing of said tubular portion.

6. A shielded hypodermic needle assembly as set forth in claim 1 wherein said cannula is a hypodermic needle and said housing has a chamber in communication with said lumen of said needle.

7. A shielded hypodermic needle assembly as set forth in claim 1 which further comprises an antimicrobial coating on a free end face of said wall.

8. A shielded hypodermic needle assembly comprising
a housing defining a chamber;
a hollow hypodermic needle mounted in and extending from said housing, said needle having a lumen in communication with said chamber; and
a one piece elastomeric shield extending from said housing in an exposed manner relative to the surrounding environment, said shield consisting of a resilient longitudinally collapsible tubular portion concentrically about said needle and a cap defining a transverse wall at a distal end to form a sealed chamber with said tubular portion to contain said needle therein in a sterile condition, said tubular portion being collapsible from an extended position about said cannula under a longitudinally applied force into a collapsed condition and being resiliently expandable into said extended position upon release of said force.

9. A shielded hypodermic needle assembly as set forth in claim 8 wherein said cap is of rigid block-like shape and said wall has a flat end face for abutting a septum of a vial containing fluid.

10. A shielded hypodermic needle assembly as set forth in claim 8 which further comprises a longitudinally split rigid sleeve portion to pevent longitudinal collapsing of said tubular portion.

11. A shielded hypodermic needle assembly as set forth in claim 8 wherein said tubular portion has a constant outside diameter and said cap has an outside diameter greater than outside diameter of said tubular portion.

12. A shielded hypodermic needle assembly as set forth in claim 11 wherein said cap has a T-shaped cross-section.

13. A shielded hypodermic needle assembly as set forth in claim 8 which further comprises an antimicrobial coating on a free end face of said wall.

14. A shielded hypodermic needle assembly comprising
a housing defining a chamber;
a hollow hypodermic needle mounted in and extending from said housing, said needle having a lumen in communication with said chamber; and
a one piece elastomeric shield extending from said housing, said shield consisting of a resilient longitudinally collapsible tubular portion concentrically about said needle and an enlarged relatively rigid cap defining a transverse wall at a distal end, said wall being sized to permit penetration of said needle therethrough in response to longitudinal collapsing of said tubular portion and resealing of said wall in response to expansion of said tubular portion and withdrawal of said needle therefrom.

15. A shielded hypodermic needle assembly as set forth in claim 14 wherein said wall has a flat end face for abutting a septum of a vial containing fluid.

16. A shielded hypodermic needle assembly as set forth in claim 14 which further comprises a longitudinally split rigid sleeve removably mounted about said tubular portion to prevent longitudinal collapsing of said tubular portion.

17. A shielded cannula assembly comprising
a cup-shaped housing for receiving a blood collecting tube;
a hub integral with said housing;
a first cannula extending from said hub;
a one piece tubular shield extending from said hub, said shield consisting of a resilient longitudinally collapsible tubular portion about said cannula and a transverse wall at a distal end for selective passage of said cannula therethrough; said wall being sized to permit penetration of said cannula therethrough in response to longitudinal collapsing of said tubular portion and resealing of said wall in response to expansion of said tubular portion and withdrawal of said cannula therefrom;
a second cannula extending from said hub and being in communication with said first cannula to pass fluid therebetween; and
a valve mounted on said hub and over said second cannula for selective passage of said second cannula therethrough into a blood collecting tube received in said housing.

18. A shielded cannula assembly comprising
a housing;
a pair of cannulae, each cannula extending from a opposite end of said housing and having a lumen in communication with a lumen of the other of said cannulae;
a pair of one piece tubular shields, each shield extending from an opposite end of said housing and consisting of a resilient longitudinally extending collapsible portion about a respective cannula and a transverse wall at a distal end for selective passage of said respective cannula therethrough, said wall being sized to permit penetration of said cannula therethrough in response to longitudinal collapsing of said tubular portion and resealing of said wall in response to expansion of said tubular portion and withdrawal of said cannula therefrom.

19. A shielded cannula assembly as set forth in claim 8 wherein said wall of said cap has an uninterrupted end face.

* * * * *